(12) United States Patent
Oosake

(10) Patent No.: US 12,009,105 B2
(45) Date of Patent: Jun. 11, 2024

(54) LEARNING APPARATUS AND LEARNING METHOD FOR TRAINING NEURAL NETWORK

(71) Applicant: FUJIFILM Corporation, Tokyo (JP)

(72) Inventor: Masaaki Oosake, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 577 days.

(21) Appl. No.: 17/197,060

(22) Filed: Mar. 10, 2021

(65) Prior Publication Data

US 2021/0216823 A1 Jul. 15, 2021

Related U.S. Application Data

(63) Continuation of application No. PCT/JP2019/033599, filed on Aug. 28, 2019.

(30) Foreign Application Priority Data

Sep. 20, 2018 (JP) ................................. 2018-176317

(51) Int. Cl.
*G06V 10/25* (2022.01)
*A61B 1/00* (2006.01)
(Continued)

(52) U.S. Cl.
CPC ....... *G16H 50/70* (2018.01); *A61B 1/000094* (2022.02); *A61B 1/000096* (2022.02);
(Continued)

(58) Field of Classification Search
CPC .............. G16H 50/70; A61B 1/000094; A61B 1/000096; A61B 1/045; G06F 18/213;
(Continued)

(56) References Cited

U.S. PATENT DOCUMENTS

| | | | | |
|---|---|---|---|---|
| 10,380,447 B1* | 8/2019 | Kulewski | ............. | G06V 10/235 |
| 2008/0232718 A1* | 9/2008 | Avinash | ................. | A61B 6/563 |
| | | | | 382/305 |

(Continued)

FOREIGN PATENT DOCUMENTS

| | | |
|---|---|---|
| JP | 6330092 | 5/2018 |
| JP | 2018096834 | 6/2018 |
| WO | 2017106645 | 6/2017 |

OTHER PUBLICATIONS

"International Search Report (Form PCT/ISA/210) of PCT/JP2019/033599," mailed on Oct. 21, 2019, with English translation thereof, pp. 1-3.

(Continued)

*Primary Examiner* — Ming Y Hon
(74) *Attorney, Agent, or Firm* — JCIPRNET

(57) ABSTRACT

There are provided a learning apparatus and a learning method that can facilitate creation of teaching data and prevent overtraining. A learning apparatus (10) includes a first database that stores a first image set in which a first image for learning and coordinate information for identifying a region larger than a region of interest included in the first image are associated with each other, and a second database that stores a second image set in which a second image for learning and second mask data for identifying a region of interest included in the second image are associated with each other. In a case of using the first image set to update a parameter of a CNN (32) (in a case of performing learning), a mask data creation unit (38) creates first mask data on the basis of the coordinate information for identifying the region larger than the region of interest. The first image and the second image are used as input images for the (Continued)

CNN (32), and the first mask data and the second mask data are used as teaching data to update the parameter of the CNN (32).

19 Claims, 8 Drawing Sheets

(51) Int. Cl.
*G06F 18/213* (2023.01)
*G06F 18/214* (2023.01)
*G06N 3/08* (2023.01)
*G06T 7/00* (2017.01)
*G06V 10/75* (2022.01)
*G06V 10/764* (2022.01)
*G06V 10/774* (2022.01)
*G06V 10/82* (2022.01)
*G16H 30/20* (2018.01)
*G16H 50/70* (2018.01)

(52) U.S. Cl.
CPC ........ *G06F 18/213* (2023.01); *G06F 18/2148* (2023.01); *G06N 3/08* (2013.01); *G06T 7/0012* (2013.01); *G06V 10/25* (2022.01); *G06V 10/758* (2022.01); *G06V 10/764* (2022.01); *G06V 10/7747* (2022.01); *G06V 10/82* (2022.01); *G16H 30/20* (2018.01); *G06T 2207/10016* (2013.01); *G06T 2207/10068* (2013.01); *G06T 2207/20081* (2013.01); *G06T 2207/20084* (2013.01); *G06T 2207/30096* (2013.01); *G06V 2201/03* (2022.01)

(58) Field of Classification Search
CPC ..... G06F 18/2148; G06N 3/08; G06T 7/0012; G06V 10/25; G06V 10/758; G06V 10/764
See application file for complete search history.

(56) References Cited

U.S. PATENT DOCUMENTS

| | | | |
|---|---|---|---|
| 2013/0278829 A1* | 10/2013 | Tegzes | H04N 21/44218 |
| | | | 348/607 |
| 2015/0117730 A1* | 4/2015 | Takayama | G02B 21/367 |
| | | | 382/128 |
| 2016/0275674 A1* | 9/2016 | Rivet-Sabourin | G06T 7/11 |
| 2017/0109881 A1* | 4/2017 | Avendi | G06T 7/11 |
| 2018/0032840 A1* | 2/2018 | Yu | G06V 10/774 |
| 2018/0061046 A1* | 3/2018 | Bozorgtabar | G06T 7/11 |
| 2018/0082420 A1* | 3/2018 | Brown | A61B 6/5205 |
| 2018/0220872 A1* | 8/2018 | Tashiro | A61B 1/000094 |
| 2018/0260604 A1* | 9/2018 | McDonald | G06T 7/0012 |
| 2018/0322632 A1* | 11/2018 | Barnes | G06T 11/60 |
| 2018/0336662 A1* | 11/2018 | Kimura | G06T 3/4053 |
| 2019/0213443 A1* | 7/2019 | Cunningham | G06N 3/08 |
| 2019/0370586 A1 | 12/2019 | Otsuki | |
| 2019/0377949 A1* | 12/2019 | Chen | G06F 18/217 |
| 2020/0029924 A1* | 1/2020 | Hamerslag | A61B 6/5264 |
| 2020/0097709 A1* | 3/2020 | Huang | G06F 18/214 |
| 2020/0167929 A1* | 5/2020 | Wang | G06T 7/0012 |
| 2020/0184647 A1* | 6/2020 | Harrison | G16H 30/40 |
| 2020/0279389 A1* | 9/2020 | McIver | G06T 7/12 |
| 2023/0257648 A1* | 8/2023 | Bao | C09K 11/65 |
| | | | 252/301.4 F |

OTHER PUBLICATIONS

"Written Opinion of the International Searching Authority (Form PCT/ISA/237) of PCT/JP2019/033599," mailed on Oct. 21, 2019, with English translation thereof, pp. 1-7.

Alex Krizhevsky et al., "ImageNet Classification with Deep Convolutional Neural Networks", NIPS, 2012, pp. 1-9.

Jonathan Long et al., "Fully Convolutional Networks for Semantic Segmentation", Computer Vision and Pattern Recognition, IEEE, Mar. 2015, pp. 1-10.

* cited by examiner

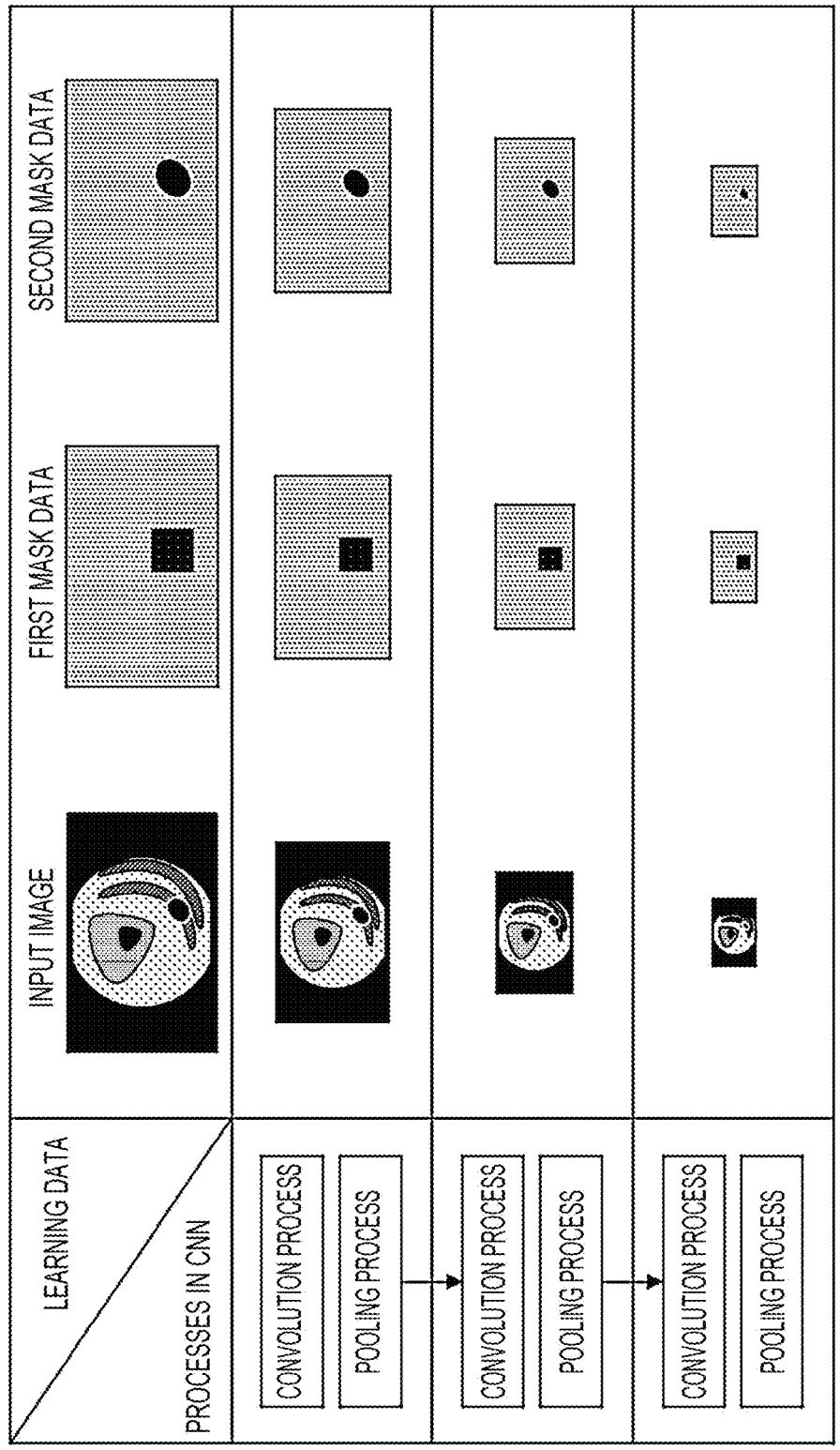

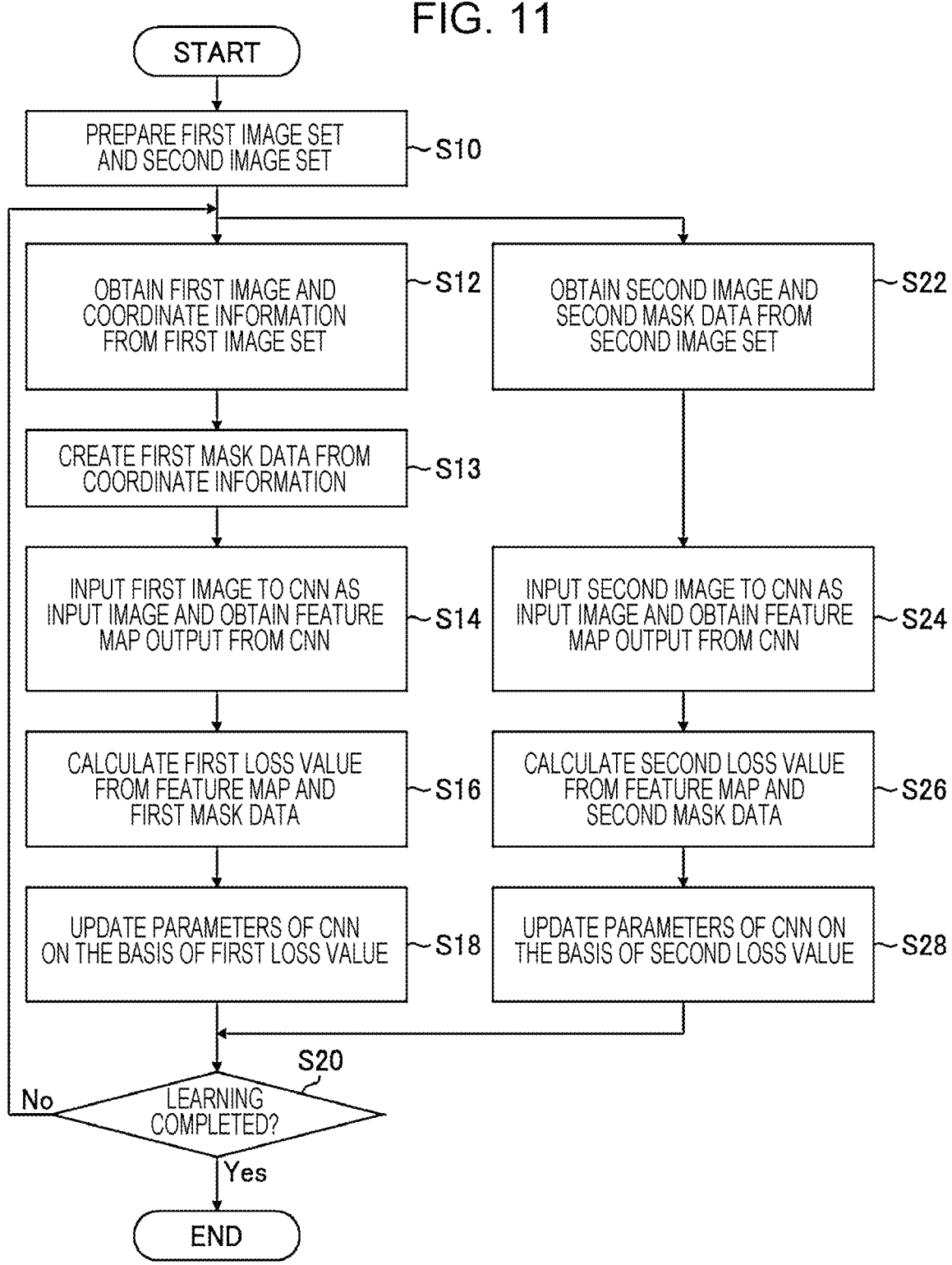

LEARNING APPARATUS AND LEARNING METHOD FOR TRAINING NEURAL NETWORK

CROSS-REFERENCE TO RELATED APPLICATIONS

The present application is a Continuation of PCT International Application No. PCT/JP2019/033599 filed on Aug. 28, 2019 claiming priority under 35 U.S.C § 119(a) to Japanese Patent Application No. 2018-176317 filed on Sep. 20, 2018. Each of the above applications is hereby expressly incorporated by reference, in its entirety, into the present application.

BACKGROUND OF THE INVENTION

1. Field of the Invention

The present invention relates to a learning apparatus and a learning method and specifically relates to a technique for identifying a desired region of interest from an input image.

2. Description of the Related Art

In recent years, in the machine learning field, deep learning using a multilayer neural network has been drawing attention. With deep learning, a neural network can semi-automatically acquire various feature representations, and therefore, engineers need not devise a method for extracting feature values. Specifically, for image recognition, a convolutional neural network (CNN) has been drawing attention (A. Krizhevsky, I. Sutskever, and G. Hinton. ImageNet classification with deep convolutional neural networks. In NIPS, 2012).

Further, a technique for separating a region on a per pixel basis by using a CNN is also known (Long J, Shelhamer E, Darrell T. Fully convolutional networks for semantic segmentation. Computer Vision and Pattern Recognition. IEEE, 2015:3431-3440).

In order to perform, in a CNN, region classification (segmentation) of a region of interest in an input image on a per pixel basis or on a per block basis, the block being formed of several pixels, it is necessary to create mask data by performing annotation for the region of interest and the other region in the input image on a per pixel basis or on a per block basis, the block being formed of several pixels, and to feed this mask data to the CNN as teaching data.

However, in learning in which classification is performed on a per pixel basis or on a per block basis, the block being formed of several pixels, parameters tend to vary to a large degree at the time of learning, which may lead to overtraining.

Overtraining refers to a state where teaching data is learned but overfitting to the teaching data results in underfitting to unknown data (a state where generalization is not attained).

To prevent such overtraining, a large amount of teaching data is necessary, and it is necessary to create a large amount of mask data by performing annotation for a region of interest and the other region in an input image on a per pixel basis or on a per block basis, the block being formed of several pixels.

To date, apparatuses that generate teaching data have been proposed (JP2018-96834A and JP6330092B).

A data processing apparatus described in JP2018-96834A automatically recognizes the type of an object, which is a target for which teaching data is generated, from an input image by a recognition processing unit and adds the result of recognition to the input image to generate teaching data, instead of visually identifying the type of the object and manually performing labeling.

A teaching data generation apparatus described in JP6330092B includes a database that stores an image-specific component of at least any one of the shape or other external appearance factors of an object extracted from an input image, a change unit that changes the image-specific component stored in the database to generate one or more types of other image-specific components, and a reconstruction unit that generates and applies to machine learning, a reconstruction image that at least partially corresponds to the input image by using the other image-specific components.

SUMMARY OF THE INVENTION

The invention described in JP2018-96834A can enable automatic labeling of objects and reduce effort to prepare a large amount of teaching data but is not intended to generate teaching data for learning for performing region classification (segmentation) for input images on a per pixel basis or on a per block basis, the block being formed of several pixels.

The invention described in JP6330092B is intended to generate various types of teaching data from one input image and, similarly to JP2018-96834A, is not intended to generate teaching data for learning for performing segmentation.

The present invention has been made in view of the above-described circumstances, and an object thereof is to provide a learning apparatus and a learning method that can facilitate creation of teaching data and prevent overtraining.

To achieve the above-described object, a learning apparatus according to an aspect of the present invention includes: a storage unit that stores a first image set in which a first image for learning and coordinate information for identifying a region larger than a region of interest included in the first image are associated with each other and a second image set in which a second image for learning and second mask data for identifying a region of interest included in the second image are associated with each other; a neural network that outputs a feature map from an input image; a first loss value calculation unit that compares a first feature map output from the neural network in response to input of the first image as the input image with first mask data created on the basis of the coordinate information associated with the first image to calculate a first loss value; a second loss value calculation unit that compares a second feature map output from the neural network in response to input of the second image as the input image with the second mask data associated with the second image to calculate a second loss value; and a parameter control unit that updates a parameter of the neural network on the basis of the first loss value and the second loss value.

According to the aspect of the present invention, to create the first image set, the first image for learning and the coordinate information for identifying the region larger than the region of interest included in the first image are associated with each other. Input of the coordinate information for identifying the region larger than the region of interest is easier than manual input of the second mask data for identifying the region of interest (for example, an operation of painting the region of interest on a per pixel basis). That is, when the first image set and the second image set are used as learning data, effort to prepare learning data (specifically, teaching data) can be significantly made smaller than in a case where only the second image set is used as learning data. Unlike the second mask data, the first mask data that is created on the basis of the coordinate information for identifying the region larger than the region of interest does not precisely indicate the region of interest. Therefore, learning using the first mask data can prevent overtraining even if the image set includes a small amount of data. Further, learning using the second mask data can enable learning in which the region of interest can be precisely recognized from the input image.

Preferably, the learning apparatus according to another aspect of the present invention further includes a mask data creation unit that creates the first mask data on the basis of the coordinate information associated with the first image, in which the mask data creation unit creates the first mask data corresponding to the first image before the first image is input to the neural network.

In the learning apparatus according to yet another aspect of the present invention, the coordinate information is information for identifying a rectangular region that includes the region of interest, and the first mask data is mask data in which the rectangular region is masked.

In the learning apparatus according to yet another aspect of the present invention, preferably, a region smaller than the rectangular region is set within the rectangular region, and the first loss value calculation unit excludes a region that is within the rectangular region and outside the region smaller than the rectangular region from loss value calculation. This is because the region that is within the rectangular region and outside the region smaller than the rectangular region (specifically, the regions in the corners of the rectangular region) is often the background region (the region other than the region of interest).

In the learning apparatus according to yet another aspect of the present invention, preferably, a region smaller than the rectangular region is set within the rectangular region, and the first loss value calculation unit excludes the region smaller than the rectangular region from loss value calculation.

In the learning apparatus according to yet another aspect of the present invention, the coordinate information is information for identifying an elliptic region that includes the region of interest, and the first mask data is mask data in which the elliptic region is masked.

In the learning apparatus according to yet another aspect of the present invention, preferably, a region smaller than the elliptic region is set within the elliptic region, and the first loss value calculation unit excludes a region that is within the elliptic region and outside the region smaller than the elliptic region from loss value calculation.

In the learning apparatus according to yet another aspect of the present invention, preferably, a region smaller than the elliptic region is set within the elliptic region, and the first loss value calculation unit excludes the region smaller than the elliptic region from loss value calculation.

In the learning apparatus according to yet another aspect of the present invention, preferably, the first loss value calculation unit compares the first feature map smaller in size than the first image with the first mask data smaller in size than the second image to calculate the first loss value, and the second loss value calculation unit compares the second feature map smaller in size than the second image with the second mask data smaller in size than the second image to calculate the second loss value. This is because the size of the first feature map and that of the second feature map become smaller than the original size of the first image and that of the second image due to a pooling process, etc. but the loss values can be calculated without restoring the sizes of the first feature map and the second feature map to sizes equal to the sizes of the first image and the second image.

A learning apparatus according to yet another aspect of the present invention includes: a storage unit that stores a first image set in which a first image for learning and first mask data for identifying a region larger than a region of interest included in the first image are associated with each other and a second image set in which a second image for learning and second mask data for identifying a region of interest included in the second image are associated with each other; a neural network that outputs a feature map from an input image; a first loss value calculation unit that compares a first feature map output from the neural network in response to input of the first image as the input image with the first mask data associated with the first image to calculate a first loss value; a second loss value calculation unit that compares a second feature map output from the neural network in response to input of the second image as the input image with the second mask data associated with the second image to calculate a second loss value; and a parameter control unit that updates a parameter of the neural network on the basis of the first loss value and the second loss value.

In the learning apparatus according to yet another aspect of the present invention, preferably, each of the first mask data and the second mask data is mask data that is subjected to a pooling process at least once. This is to adjust the sizes of the first mask data and the second mask data to the sizes of the first feature map and the second feature map.

In the learning apparatus according to yet another aspect of the present invention, preferably, the neural network has at least one pooling layer, and each of the first mask data and the second mask data is mask data that is subjected to a pooling process corresponding to the pooling layer.

In the learning apparatus according to yet another aspect of the present invention, preferably, in the first image set, the first image that includes a blur is present. The use of the first image including a blur can further prevent overtraining.

In the learning apparatus according to yet another aspect of the present invention, preferably, the first image that constitutes the first image set and the second image that constitutes the second image set are medical images. The medical images include endoscopic images, X-ray images, CT (computed tomography) images, MRI (magnetic resonance imaging) images, and so on.

In the learning apparatus according to yet another aspect of the present invention, preferably, the first image that constitutes the first image set is an image extracted from a moving image. This is because a large number of first images can be obtained and a moving image includes an image having a blur.

In the learning apparatus according to yet another aspect of the present invention, the first image that constitutes the first image set and the second image that constitutes the second image set are images captured by an endoscope apparatus.

In the learning apparatus according to yet another aspect of the present invention, preferably, the second mask data is mask data in which a lesion region included in the second image is masked.

A learning method according to yet another aspect of the present invention includes: a step of preparing a first image set in which a first image for learning and coordinate information for identifying a region larger than a region of interest included in the first image are associated with each other and a second image set in which a second image for learning and second mask data for identifying a region of interest included in the second image are associated with each other; a step of comparing a first feature map output from a neural network in response to input of the first image as an input image for the neural network with first mask data created on the basis of the coordinate information associated with the first image to calculate a first loss value; a step of comparing a second feature map output from the neural network in response to input of the second image as an input image for the neural network with the second mask data associated with the second image to calculate a second loss value; and a step of updating a parameter of the neural network on the basis of the first loss value and the second loss value.

A learning method according to yet another aspect of the present invention includes: a step of preparing a first image set in which a first image for learning and first mask data for identifying a region larger than a region of interest included in the first image are associated with each other and a second image set in which a second image for learning and second mask data for identifying a region of interest included in the second image are associated with each other; a step of comparing a first feature map output from a neural network in response to input of the first image as an input image for the neural network with the first mask data associated with the first image to calculate a first loss value; a step of comparing a second feature map output from the neural network in response to input of the second image as an input image for the neural network with the second mask data associated with the second image to calculate a second loss value; and a step of updating a parameter of the neural network on the basis of the first loss value and the second loss value.

According to the present invention, the first image set and the second image set are used as learning data. Therefore, it is not necessary to create the second image set including a large amount of data accompanied by mask data obtained by performing annotation for a region of interest and the other region in the second image on a per pixel basis or on a per block basis, the block being formed of several pixels. Further, effort to prepare learning data can be significantly made smaller than in a case where only the second image set is used as learning data, and overtraining can be prevented.

BRIEF DESCRIPTION OF THE DRAWINGS

FIG. 10 is a schematic diagram illustrating a state where the size of a feature map gradually decreases relative to the size of an input image each time a pooling process is performed in a CNN; and FIG. 11 is a flowchart illustrating an embodiment of an image learning method according to the present invention.

DESCRIPTION OF THE PREFERRED EMBODIMENTS

Hereinafter, preferred embodiments of the learning apparatus and the learning method according to the present invention will be described with reference to the attached drawings.

Hardware Configuration of Learning Apparatus

Figure 1:
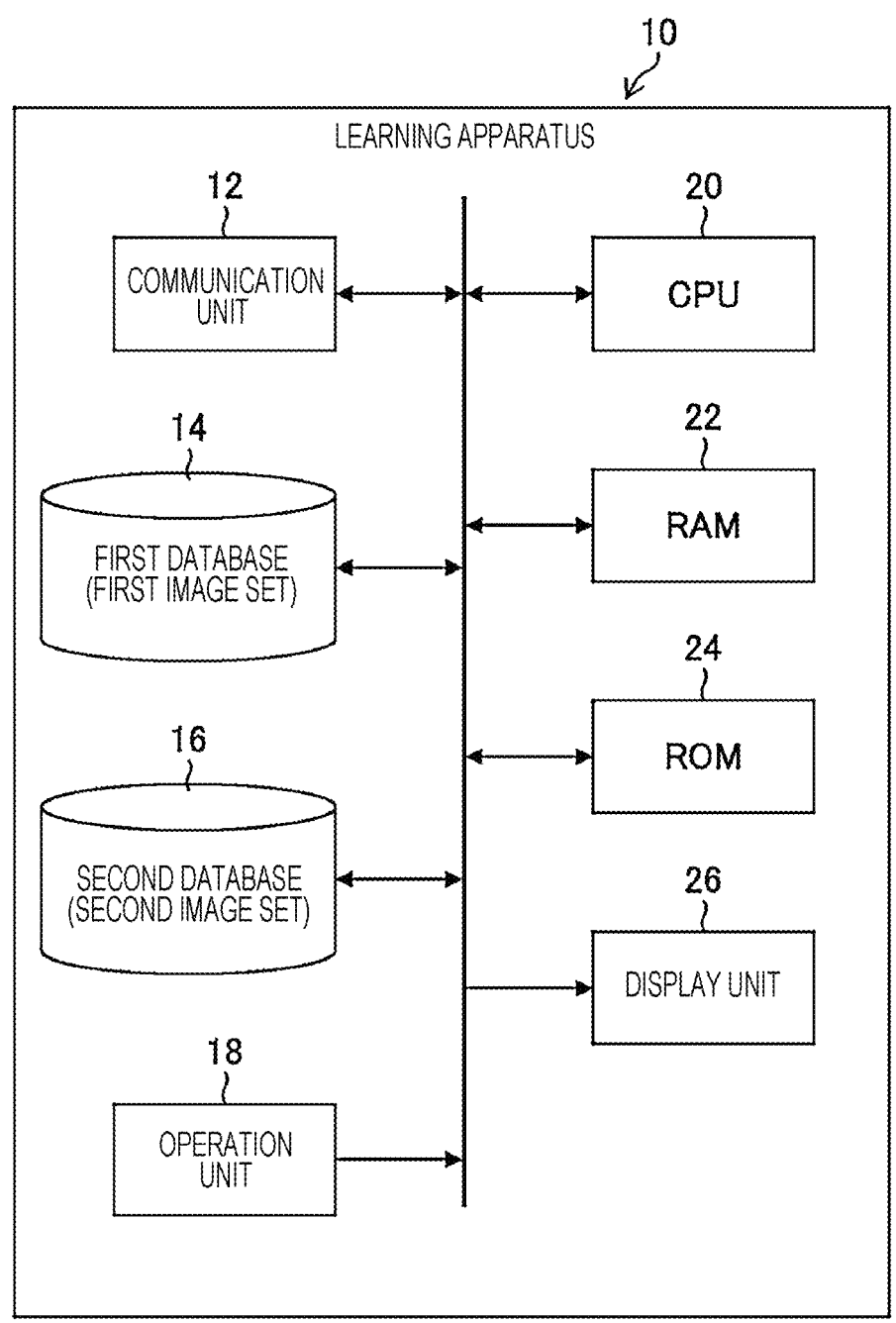
FIG. 1 is a block diagram illustrating an example hardware configuration of a learning apparatus according to the present invention.

FIG. 1 is a block diagram illustrating an example hardware configuration of the learning apparatus according to the present invention.

A learning apparatus 10 illustrated in FIG. 1 performs learning so as to function as a recognizer for performing region classification (segmentation) of a region of interest in an input image on a per pixel basis or on a per block basis, the block being formed of several pixels. The learning apparatus 10 can be formed of a personal computer or a workstation.

The learning apparatus 10 of this example is mainly constituted by a communication unit 12, a large-capacity storage or a first database 14 and a second database 16, an operation unit 18, a CPU (central processing unit) 20, a RAM (random access memory) 22, a ROM (read-only memory) 24, and a display unit 26.

The communication unit 12 is a unit that performs a process of communicating with an external apparatus by wire or wirelessly to exchange information with the external apparatus.

The first database 14 and the second database 16 that function as a storage unit respectively store a first image set and a second image set for learning.

The first image set is a set of pieces of learning data in each of which a first image for learning and coordinate information for identifying a region larger than a region of interest included in the first image are associated with each other. The second image set is a set of pieces of learning data in each of which a second image for learning and second mask data for identifying a region of interest included in the second image are associated with each other.

Figure 2:
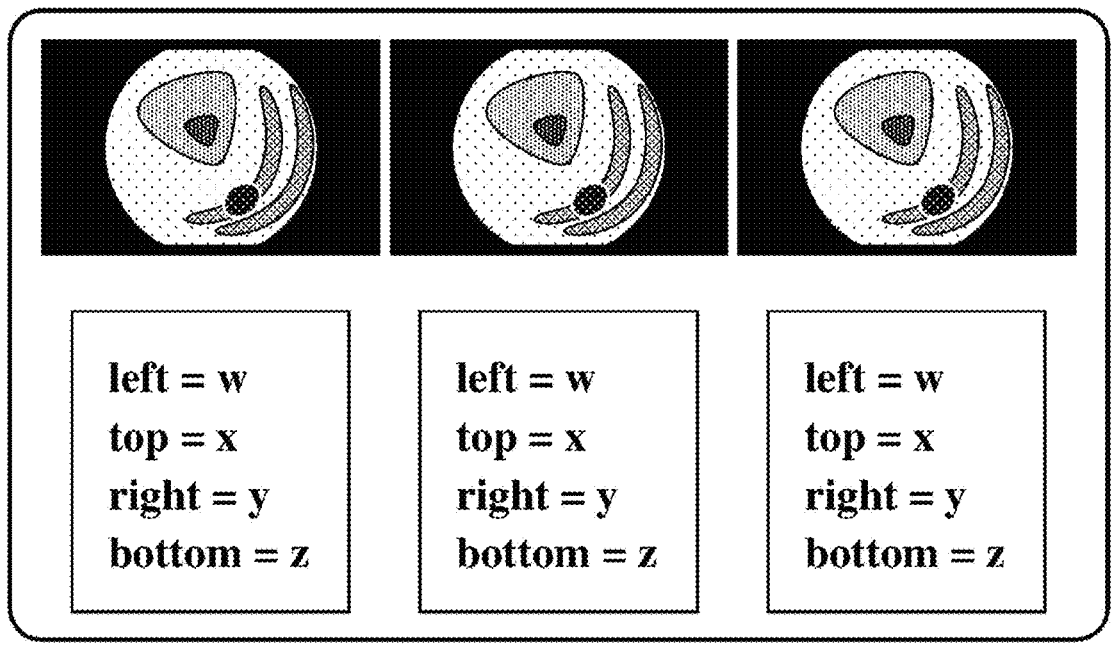
FIG. 2 is a diagram illustrating an example of a first image set stored in a first database 14.

FIG. 2 is a diagram illustrating an example of the first image set stored in the first database 14 and illustrates a case where first images (medical images) captured by an endoscope apparatus are used as input images for the learning apparatus 10.

As illustrated in FIG. 2, the first image set is a set of pieces of learning data in each of which a first image (images illustrated in the upper part of FIG. 2), which is an input image for the learning apparatus 10 at the time of learning, and coordinate information (pieces of coordinate information illustrated in the lower part of FIG. 2), which is used to create mask data that serves as teaching data for the first image, are paired and stored.

Figure 3:
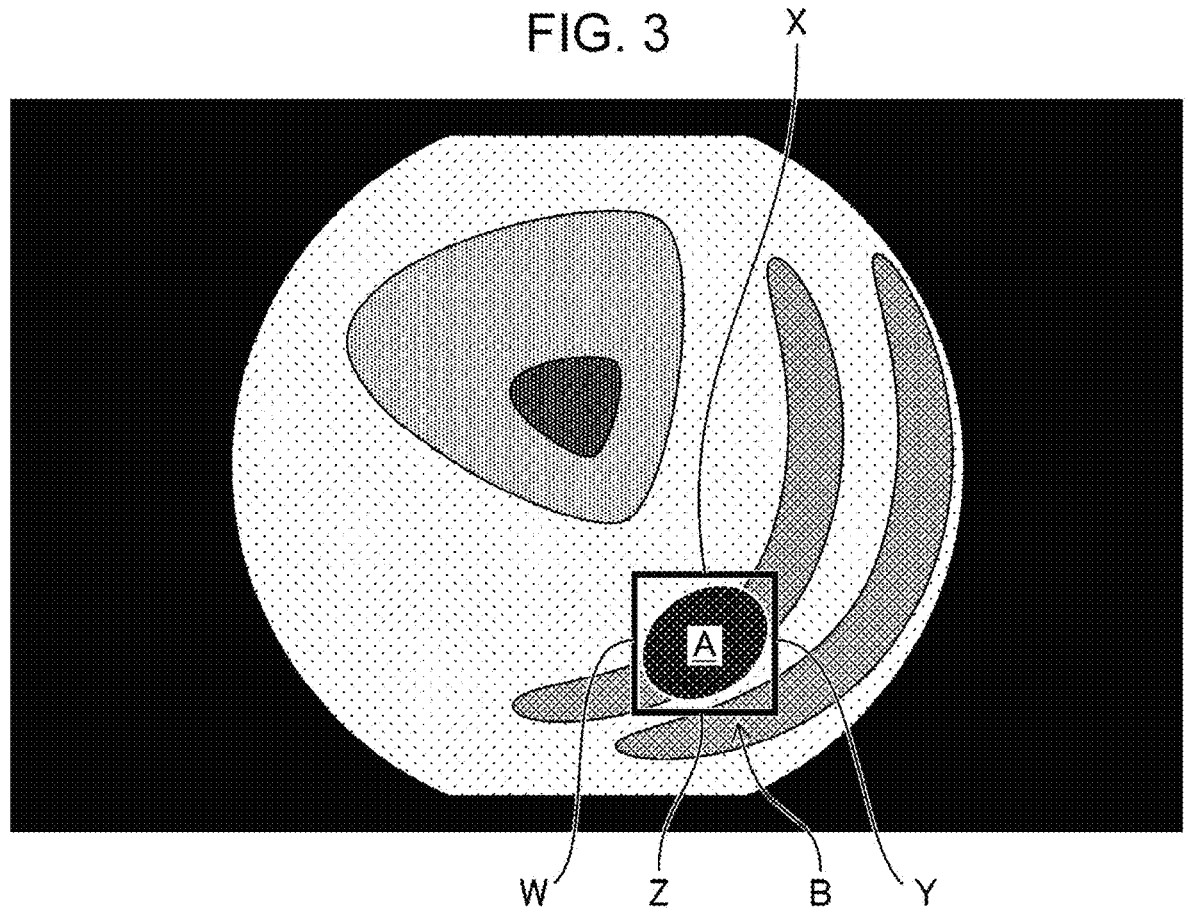
FIG. 3 is a diagram illustrating an image (first image) captured by an endoscope apparatus and a rectangular region B.

Here, the coordinate information is coordinate information for identifying a rectangular region B larger than a region of interest A, which is, for example, a lesion region, included in the first image as illustrated in FIG. 3. The coordinate information of this example has a coordinate (left=w) indicating the left side of the rectangular region B including the region of interest A, a coordinate (top=x) indicating the top side thereof, a coordinate (right=y) indicating the right side thereof, and a coordinate (bottom=z) indicating the bottom side thereof.

Figure 4:
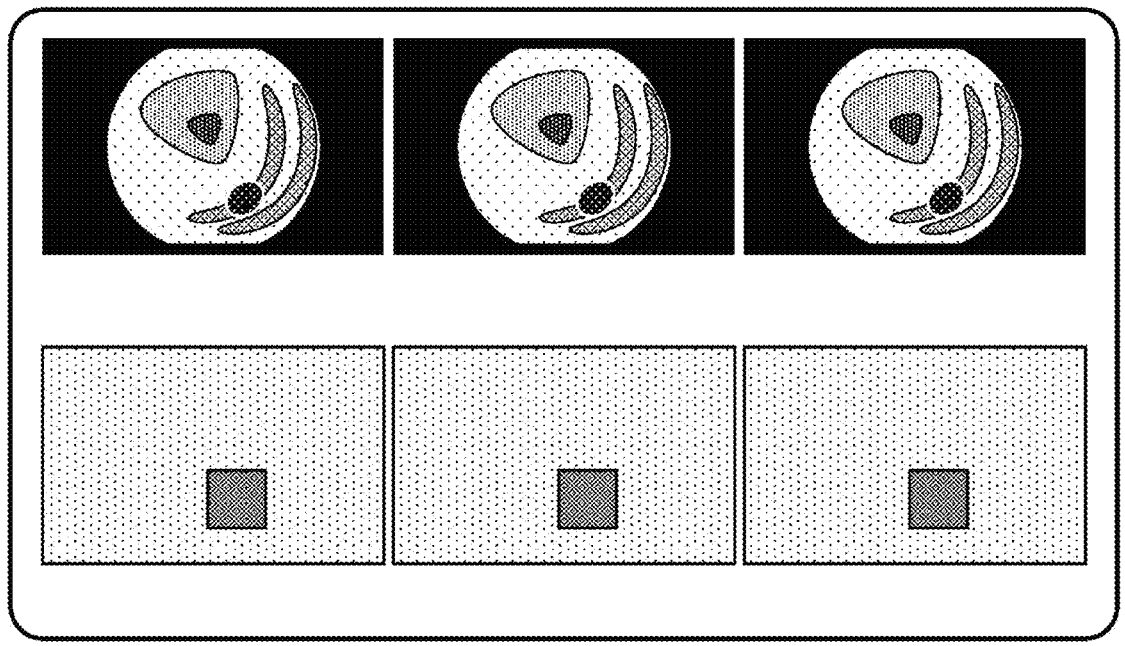
FIG. 4 is a diagram for explaining first mask data that is created from coordinate information illustrated in FIG. 2.

The coordinate information associated with the first image is used to create mask data (first mask data) illustrated in the lower part of FIG. 4. The first mask data is mask data in which the rectangular region including the region of interest is masked on a per pixel basis or on a per block basis, the block being formed of several pixels. For example, "1" is assigned to pixels within the rectangular region and "0" is assigned to pixels in the background region (the region other than the rectangular region) to thereby obtain binary image data.

Coordinate information for identifying a region larger than the region of interest A included in a first image can be input in such a manner that, for example, the first image is displayed on the display unit 26 and a user operates the operation unit 18 (a pointing device, such as a mouse) to display a rectangular frame (see FIG. 3) that surrounds the region of interest A on the display unit 26 and to fix the position and size of the rectangular frame.

Figure 5:
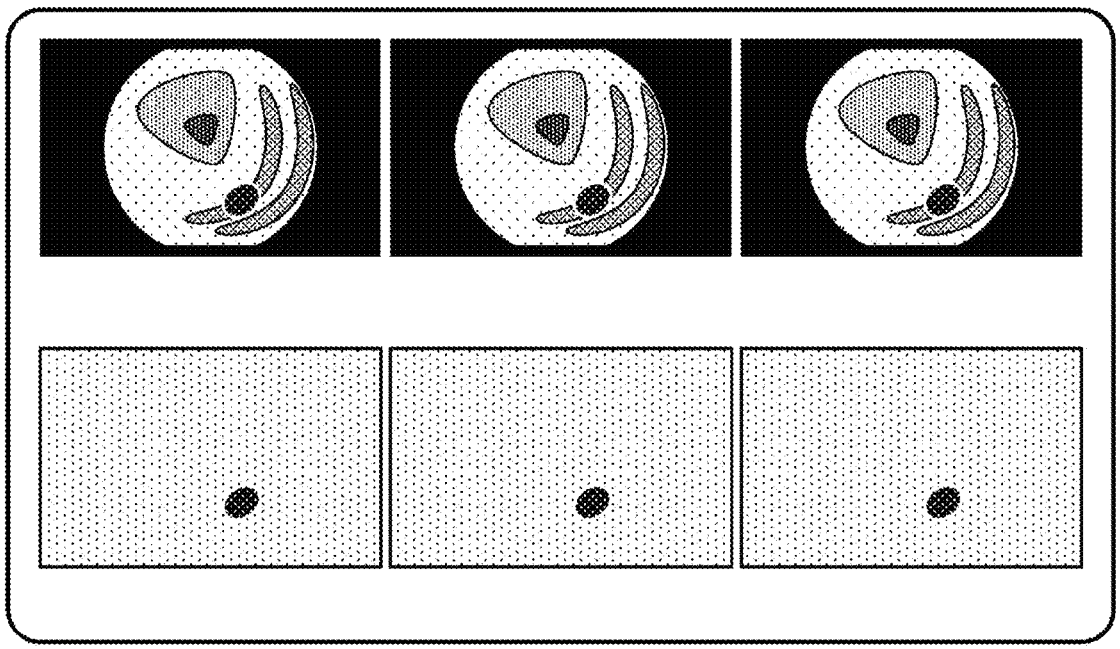
FIG. 5 is a diagram illustrating an example of a second image set stored in a second database 16.

FIG. 5 is a diagram illustrating an example of the second image set stored in the second database 16 and illustrates a case where second images (medical images) captured by an endoscope apparatus are used as input images for the learning apparatus 10.

As illustrated in FIG. 5, the second image set is a set of pieces of learning data in each of which a second image (images illustrated in the upper part of FIG. 5), which is an input image for the learning apparatus 10 at the time of learning, and mask data (pieces of second mask data illustrated in the lower part of FIG. 5), which serves as teaching data for the second image, are paired and stored.

The second mask data is mask data in which the region of interest (for example, a lesion region) included in the second image is masked on a per pixel basis or on a per block basis, the block being formed of several pixels.

Second mask data for identifying the region of interest A included in a second image can be created in such a manner that, for example, the second image is displayed on the display unit 26 and a user operates the operation unit 18 (a pointing device, such as a mouse) to draw the outline of the region of interest A on a per pixel basis or on a per block basis, the block being formed of several pixels, or to paint the region of interest A on a per pixel basis or on a per block basis, the block being formed of several pixels.

Input of coordinate information by a user is easier than creation of second mask data. Therefore, the first image set that is stored in the first database 14 can be created more easily than the second image set that is stored in the second database 16. Accordingly, effort made by the user can be significantly made smaller than in a case of preparing the second image set including a large amount of data.

First mask data created from coordinate information is not intended to precisely identify the region of interest on a per pixel basis, and therefore, overtraining is unlikely to occur in learning in which the first image set is used, which is an advantage. Further, to prevent overtraining, it is preferable that a first image including a blur be present in the first image set.

In the first image set, a first image that includes a blur may be present, and therefore, for example, the first image may be an image extracted from a moving image captured while an endoscope is moving. When first images are extracted from a moving image, a number of first images larger than the number of second images can be collected.

Note that in this example, the first database 14 and the second database 16 are included in the learning apparatus 10; however, the first database 14 and the second database 16 may be externally provided databases. In this case, the first image set and the second image set for learning can be obtained from the external databases via the communication unit 12.

As the operation unit 18, for example, a keyboard and a mouse that are connected to the computer by wire or wirelessly are used to accept various types of operation input for machine learning.

The CPU 20 reads various programs (including a learning program that is used in machine learning) stored in, for example, the ROM 24 or a hard disk apparatus not illustrated and performs various processes. The RAM 22 is used as a workspace for the CPU 20 and is used as a storage unit that temporarily stores the read programs and various types of data.

As the display unit 26, various monitors including a liquid crystal monitor that can be connected to the computer are used, and the display unit 26 and the operation unit 18 are used as part of the user interface.

The learning apparatus 10 thus configured functions as the learning apparatus as described below by the CPU 20 reading the learning program stored in, for example, the ROM 24 or the hard disk apparatus and executing the learning program in accordance with an instruction input via the operation unit 18.

Embodiment of Learning Apparatus

Figure 6:
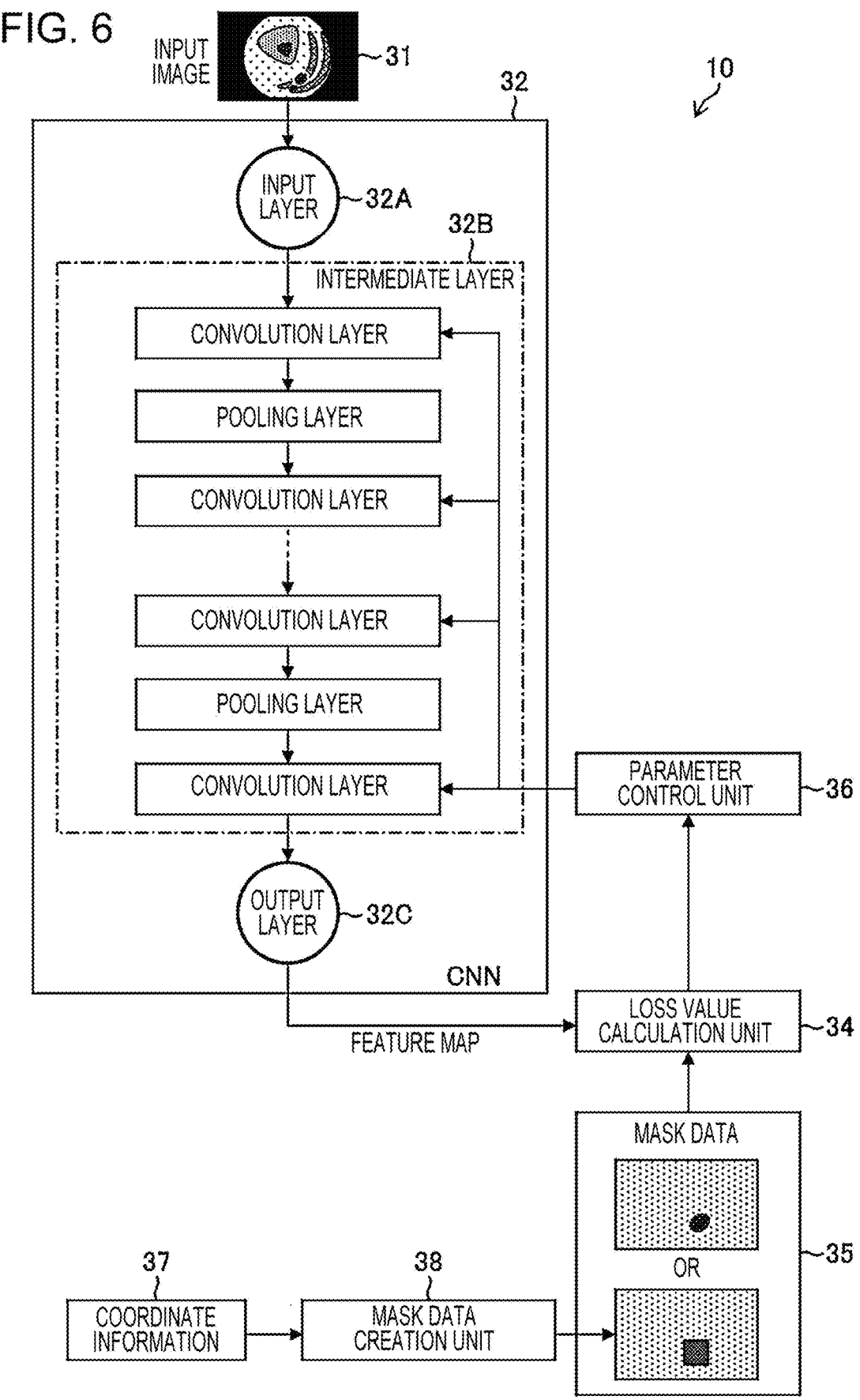
FIG. 6 is a block diagram illustrating an embodiment of a learning apparatus 10 according to the present invention.

FIG. 6 is a block diagram illustrating an embodiment of the learning apparatus 10 according to the present invention and is a functional block diagram illustrating major functions of the learning apparatus 10 illustrated in FIG. 1.

The learning apparatus 10 illustrated in FIG. 6 performs learning by using the first image set saved in the first database 14 and the second image set saved in the second database 16 to generate a learning model for performing region classification (segmentation) of a region of interest from an input image. In this example, a convolutional neural network (CNN), which is one type of learning model, is built.

The learning apparatus 10 illustrated in FIG. 6 is mainly constituted by a CNN 32, a loss value calculation unit 34, a parameter control unit 36, and a mask data creation unit 38.

In a case where, for example, an image (medical image) captured by an endoscope apparatus is used as an input image, the CNN 32 is a part corresponding to a recognizer that recognizes a region of interest, such as a lesion region, present in the input image, has a multilayer structure, and retains a plurality of weight parameters. The weight parameters are, for example, filter factors of filters that are called kernels and used in a convolution operation in a convolution layer.

When the weight parameters are updated from their initial values to optimum values, the CNN 32 can change from an untrained model to a trained model.

The CNN 32 includes an input layer 32A, an intermediate layer 32B having a plurality of sets each formed of a convolution layer and a pooling layer, and an output layer 32C, and each layer has a structure in which a plurality of "nodes" are connected by "edges".

To the input layer 32A, an input image 31 that is a learning target is input.

The intermediate layer 32B has a plurality of sets each formed of a convolution layer and a pooling layer and is a part that extracts features from an image input from the input layer 32A. The convolution layer performs a filtering process for a nearby node in the preceding layer (performs a convolution operation using the filters) to obtain a "feature map". The pooling layer reduces the feature map output from the convolution layer to obtain a new feature map. The "convolution layer" assumes a role of feature extraction, such as extraction of edges from an image, and the "pooling layer" assumes a role of providing robustness such that extracted features are not affected by, for example, translation.

Note that the intermediate layer 32B need not have the sets each formed of the convolution layer and the pooling layer and may include successive convolution layers, an activation process by an activation function, or a normalization layer.

The output layer 32C is a part that outputs a feature map representing features extracted by the intermediate layer 32B. In the CNN 32 that has been trained, for example, the output layer 32C outputs the result of recognition obtained by performing region classification (segmentation) of a region of interest, such as a lesion region, present in the input image on a per pixel basis or on a per block basis, the block being formed of several pixels.

The factors or offset values of the filters to be applied to each convolution layer of the CNN 32 that has not yet been trained are set to desired initial values.

The loss value calculation unit 34 that functions as a first loss value calculation unit and a second loss value calculation unit compares a feature map output from the output layer 32C of the CNN 32 with mask data (first mask data or second mask data) that is teaching data for the input image (first image or second image) to calculate an error between the feature map and the mask data (a loss value that is the value of a loss function). As the method for calculating the loss value, for example, softmax cross entropy or sigmoid can be used.

The parameter control unit 36 adjusts the weight parameters of the CNN 32 by using the backpropagation method on the basis of the loss value (first loss value or second loss value) calculated by the loss value calculation unit 34.

This process of parameter adjustment is repeatedly performed, and learning is repeated until the difference between the output of the CNN 32 and the mask data that is teaching data becomes small.

In a case where one piece of learning data or a plurality of pieces (one batch) of learning data to be used in learning is obtained from the first image set saved in the first database 14 and the obtained learning data is used to perform learning, before a first image that constitutes the learning data is input to the CNN 32, the mask data creation unit 38 creates first mask data on the basis of coordinate information 37 associated with the first image to be input to the CNN 32.

The coordinate information 37 of this example is coordinate information that indicates the four sides (the left side, the top side, the right side, and the bottom side) of a rectangular region that includes the region of interest A as illustrated in FIG. 3, and the mask data creation unit 38 creates first mask data in which the rectangular region is masked (the rectangular region and the background region are classified as separate regions) on the basis of the coordinate information about the four sides. The first mask data is teaching data for the first image that is an input image. Note that coordinate information for identifying a rectangular region is not limited to coordinate information indicating the four sides of the rectangular region and may be, for example, coordinates that indicate two diagonal vertices of the rectangular region.

The learning apparatus 10 as configured above uses the first image set in the first database 14 and the second image set stored in the second database 16 to perform learning. There may be a case where the learning apparatus 10 alternately uses learning data included in the first image set and learning data included in the second image set or mixes and uses learning data included in the first image set and learning data included in the second image set as appropriate to perform learning, or there may be case where the learning apparatus 10 uses learning data included in the first image set to perform learning, and thereafter, uses learning data included in the second image set to perform learning.

In a case where the CNN 32 performs learning on the basis of learning data included in the first image set stored in the first database 14, before a first image that constitutes the learning data obtained from the first database 14 is input to the CNN 32 (input layer 32A) as the input image 31, the mask data creation unit 38 creates first mask data on the basis of the coordinate information 37 associated with the first image and assumes the first mask data to be mask data 35.

Thereafter, the first image is input to the CNN 32, and a feature map that is output from the output layer 32C of the CNN 32 is added to the loss value calculation unit 34.

To the loss value calculation unit 34, the first mask data created by the mask data creation unit 38 is added, and the loss value calculation unit 34 that functions as the first loss value calculation unit compares the input feature map (first feature map) with the first mask data to calculate a loss value (first loss value).

The parameter control unit 36 adjusts the weight parameters of the CNN 32 by using the backpropagation method on the basis of the first loss value calculated by the loss value calculation unit 34. In the backpropagation method, the error is propagated backward from the last layer through layers sequentially, the stochastic gradient descent method is used in each layer, and the parameters are repeatedly updated until the error is converged.

Next, in a case where the CNN 32 performs learning on the basis of learning data included in the second image set stored in the second database 16, a second image that constitutes the learning data obtained from the second database 16 is input to the CNN 32 (input layer 32A) as the input image 31. A feature map that is output from the output layer 32C of the CNN 32 is added to the loss value calculation unit 34.

To the loss value calculation unit 34, second mask data associated with the second image input to the CNN 32 is added, and the loss value calculation unit 34 that functions as the second loss value calculation unit calculates a loss value (second loss value) on the basis of the input feature map (second feature map) and the second mask data.

The parameter control unit 36 adjusts the weight parameters of the CNN 32 by using the backpropagation method on the basis of the second loss value calculated by the loss value calculation unit 34.

When the learning apparatus 10 repeats learning using learning data in the first image set and learning using learning data in the second image set described above, the CNN 32 becomes a trained model and outputs the result of recognition in which region classification of a region of interest is performed on a per pixel basis or on a per block basis, the block being formed of several pixels, for an unknown input image.

In the learning apparatus 10, not only the second image set but also the first image set is used as learning data, and therefore, even if the second image set including a large amount of data is not used, overtraining hardly occurs, and a learning model that outputs the result of recognition equivalent to that obtained in a case where the second image set including a large amount of data is used can be generated.

Learning data in the first image set can be created by specifying coordinate information for identifying a region larger than a region of interest included in the first image and can be created more easily than learning data in the second image set for which mask data (second mask data) for identifying a region of interest included in the image needs to be created as teaching data.

The learning apparatus 10 is configured to receive a set of first image and coordinate information (first image set) but may be configured to receive a set of first image and mask data (first mask data).

Another Embodiment of First Image Set

Learning data in the first image set illustrated in FIG. 2 has coordinate information associated with a first image for identifying a rectangular region larger than the region of interest A included in the first image; however, the coordinate information is not limited to this and may be coordinate information for identifying, for example, an elliptic region larger than the region of interest.

Figure 7:
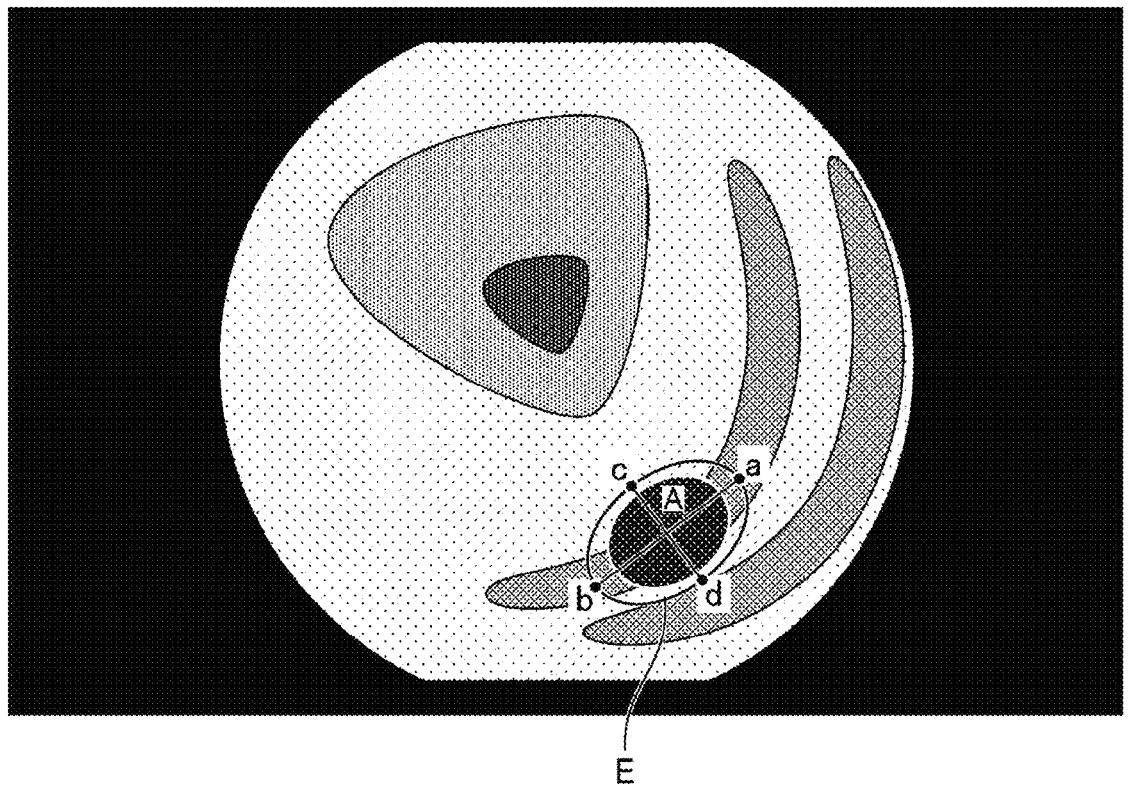
FIG. 7 is a diagram illustrating an image (first image) captured by an endoscope apparatus and an elliptic region E.

FIG. 7 is a diagram illustrating an image (first image) captured by an endoscope apparatus and an elliptic region E. The elliptic region E is a region that includes the region of interest A included in the first image and is larger than the region of interest A.

It is preferable to determine the direction of the elliptic region E such that the longer-axis direction of the elliptic region E coincides with a direction in which the region of interest A is longest.

As coordinate information for identifying the elliptic region E, coordinate information about the both ends (a, b) of the longer axis of the elliptic region E and coordinate information about the both ends (c, d) of the shorter axis thereof as illustrated in FIG. 7 can be used.

Another Embodiment of First Mask Data

The first mask data illustrated in FIG. 4 is mask data in which the rectangular region identified with the coordinate information illustrated in FIG. 2 is masked. The first mask data can be mask data in which a region smaller than the rectangular region is set within the rectangular region, and a region that is within the rectangular region and outside the region smaller than the rectangular region is excluded from loss value calculation by the loss value calculation unit 34 that functions as the first loss value calculation unit.

Figure 8:
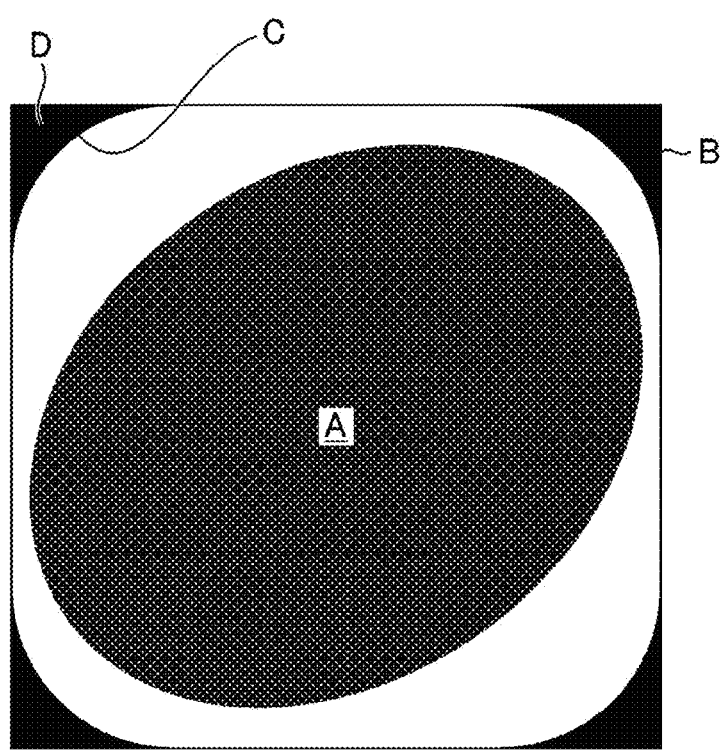
FIG. 8 is a diagram for explaining another embodiment of the first mask data.

As illustrated in FIG. 8, within the rectangular region B that includes the region of interest A, a region C smaller than the rectangular region B is set. The region C is also a region that includes the region of interest A.

A region D (which corresponds to regions in the four corners of the rectangular region B in FIG. 8) that is within the rectangular region B and outside the region C smaller than the rectangular region B is excluded in loss value calculation by the loss value calculation unit 34.

For example, "1" is assigned to pixels within the region C smaller than the rectangular region B, "0" is assigned to pixels in the background region (the region outside the rectangular region B), and "−1" is assigned to pixels in the region D that is within the rectangular region B and outside the region C smaller than the rectangular region B to thereby obtain three-value image data.

The loss value calculation unit 34 excludes the pixels within the region D assigned "−1" from loss value calculation.

In a case where the region C that is within the rectangular region B and smaller than the rectangular region B is a round region or an elliptic region that includes the region of interest A, coordinate information for identifying the region C can be information that indicates the round region or the elliptic region. In a case where the region C that is within the rectangular region B and smaller than the rectangular region B is an octagonal region including the region of interest A and obtained by removing the four corners of the rectangular region B, coordinate information for identifying the region C can be information that indicates the octagonal region.

Figure 9:
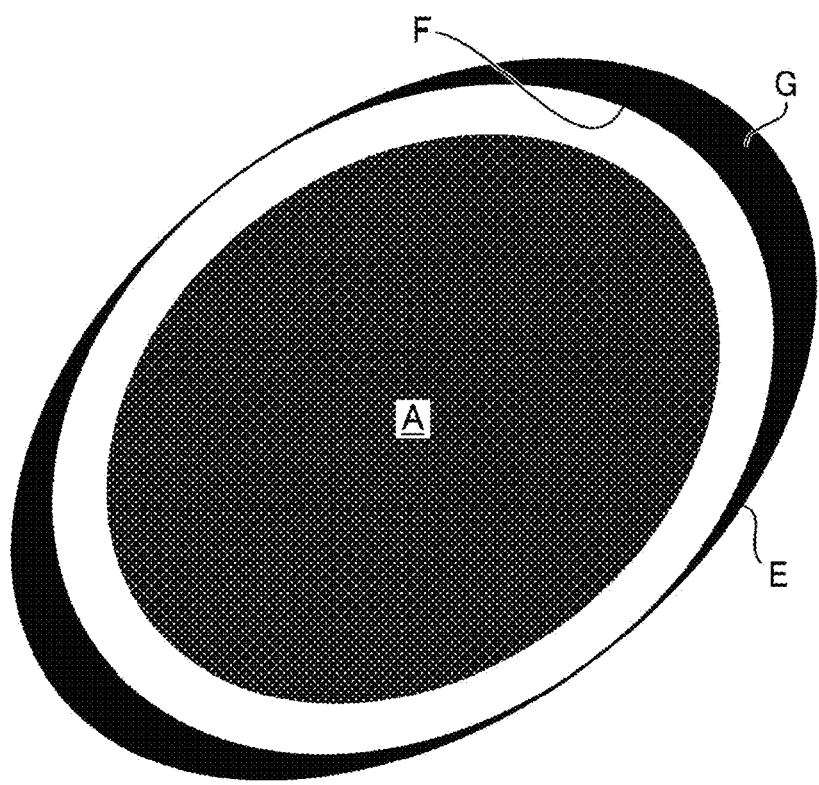
FIG. 9 is a diagram for explaining yet another embodiment of the first mask data.

In a case where first mask data is mask data in which the elliptic region E is masked (FIG. 7), a region F smaller than the elliptic region E is set within the elliptic region E as illustrated in FIG. 9. The mask data can be such that a region that is within the elliptic region E and outside the region F smaller than the elliptic region E is excluded from loss value calculation by the loss value calculation unit 34 that functions as the first loss value calculation unit.

For example, "1" is assigned to pixels within the region F smaller than the elliptic region E, "0" is assigned to pixels in the background region (the region outside the elliptic region E), and "−1" is assigned to pixels in a region G that is within the elliptic region E and outside the region F smaller than the elliptic region E to thereby obtain three-value image data.

The loss value calculation unit 34 excludes the pixels within the region G assigned "−1" from loss value calculation.

In a case where the region F that is within the elliptic region E and smaller than the elliptic region E is another elliptic region or a round region that includes the region of interest A, coordinate information for identifying the region G can be information that indicates the other elliptic region or the round region.

The first mask data described with reference to FIG. 8 is mask data for region classification of the region C smaller than the rectangular region B, the region outside the rectangular region B, and the region D that is within the rectangular region B and outside the region C smaller than the rectangular region B. As the first mask data, mask data can be created in which the region C smaller than the rectangular region B is set within the rectangular region B so as to exclude the region C smaller than the rectangular region B from loss value calculation by the loss value calculation unit 34. In this case, the region assigned "−1" and the region assigned "1" in the first mask data described with reference to FIG. 8 change places.

Similarly, the first mask data described with reference to FIG. 9 is mask data for region classification of the region F smaller than the elliptic region E, the region outside the elliptic region E (background region), and the region G that is within the elliptic region E and outside the region F smaller than the elliptic region E. As the first mask data, mask data can be created in which the region F smaller than the elliptic region E is set within the elliptic region E so as to exclude the region F smaller than the elliptic region E from loss value calculation by the loss value calculation unit 34.

Modification of Learning Apparatus

The learning apparatus 10 of the present embodiment performs a deconvolution process or an enlarging process such that output of the CNN 32 has the size of the input image. In a modification of the learning apparatus, an enlarging process, etc. is not performed, and a feature map having a size smaller than the size of the input image due to a pooling process performed once or more is output as is.

FIG. 10 is a schematic diagram illustrating a state where the size of a feature map gradually decreases relative to the size of an input image each time a pooling process is performed in the CNN.

In the modification of the learning apparatus, first mask data and second mask data having a size equal to the size of a feature map output from the output layer of the CNN (a feature map that is not subjected to an enlarging process for keeping the size of the input image) are created.

In this case, when a process the same as the pooling process in the CNN is performed (when a pooling process is performed at least once) for the first mask data or the second mask data having a size equal to the size of the input image, the first mask data or the second mask data can have a size equal to the size of the feature map output from the output layer of the CNN.

The loss value calculation unit 34 can calculate a loss value on the basis of the feature map that is output from the CNN and that is not subjected to an enlarging process and on the basis of the first mask data or the second mask data that is reduced in size as a result of a pooling process performed at least once.

Learning Method

FIG. 11 is a flowchart illustrating an embodiment of the image learning method according to the present invention and illustrates a processing procedure by the units of the learning apparatus 10 illustrated in FIG. 6.

In the first database 14 and in the second database 16, the first image set and the second image set for learning are respectively stored (step S10 of preparing image sets).

In a case where learning data in the first image set is used to perform learning, the flow proceeds to step S12. In a case where learning data in the second image set is used to perform learning, the flow proceeds to step S22. It is assumed that whether learning data in the first image set is used or learning data in the second image set is used is determined in advance by a program.

In step S12, one piece or one batch of learning data is obtained from the first image set. The learning data obtained from the first image set includes a first image to be used as an input image at the time of learning and coordinate information for creating first mask data to be used as teaching data (see FIG. 2).

The mask data creation unit 38 of the learning apparatus 10 illustrated in FIG. 6 creates first mask data on the basis of the coordinate information obtained in step S12 (step S13).

Subsequently, the first image obtained in step S12 is input to the CNN 32 as the input image 31 to obtain a feature map output from the CNN 32 (step S14).

The loss value calculation unit 34 compares the feature map obtained in step S14 with the first mask data created in step S13 to calculate a loss value (first loss value) (step S16).

The parameter control unit 36 adjusts (updates) the weight parameters of the CNN 32 by using the backpropagation method on the basis of the first loss value calculated by the loss value calculation unit 34 (step S18). The process from step S14 to step S18 is repeated until the error is converged, thereby repeatedly updating the parameters.

Subsequently, it is determined whether desired learning using the first image set and the second image set is completed (step S20). If it is determined that the desired learning is not completed (in a case of "No"), the flow proceeds to step S12 or step S22.

In a case where learning data in the second image set is used to perform learning, the flow proceeds to step S22.

In step S22, one piece or one batch of learning data is obtained from the second image set. The learning data obtained from the second image set includes a second image to be used as an input image at the time of learning and second mask data to be used as teaching data (see FIG. 5).

Next, the second image obtained in step S22 is input to the CNN 32 as the input image 31 to obtain a feature map output from the CNN 32 (step S24).

The loss value calculation unit 34 compares the feature map obtained in step S24 with the second mask data obtained in step S22 to calculate a loss value (second loss value) (step S26).

The parameter control unit 36 adjusts (updates) the weight parameters of the CNN 32 by using the backpropagation method on the basis of the second loss value calculated by the loss value calculation unit 34 (step S28). The process from step S24 to step S28 is repeated until the error is converged, thereby repeatedly updating the parameters.

Thereafter, if it is determined in step S20 that desired learning using the first image set and the second image set is completed (in a case of "Yes"), the process according to this learning method ends.

Others

The hardware configuration of the learning apparatus 10 of the present embodiment for performing various types of control is implemented as various processors as described below. The various processors include a CPU (central processing unit), which is a general-purpose processor executing software (program) to function as various control units, a programmable logic device (PLD), such as an FPGA (field-programmable gate array), which is a processor having a circuit configuration that is changeable after manufacture, and a dedicated electric circuit, such as an ASIC (application-specific integrated circuit), which is a processor having a circuit configuration specifically designed to perform specific processing.

One control unit may be configured as one of the various processors or two or more processors of the same type or different types (for example, a plurality of FPGAs or a combination of a CPU and an FPGA). Further, a plurality of control units may be configured as one processor. As the first example of configuring a plurality of control units as one processor, a form is possible where one processor is configured as a combination of one or more CPUs and software, and the processor functions as the plurality of control units, a representative example of which is a computer, such as a client or a server. As the second example thereof, a form is possible where a processor is used in which the functions of the entire system including the plurality of control units are implemented as one IC (integrated circuit) chip, a representative example of which is a system on chip (SoC). As described above, regarding the hardware configuration, the various control units are configured by using one or more of the various processors described above.

Further, the hardware configuration of the various processors is more specifically an electric circuit (circuitry) in which circuit elements, such as semiconductor elements, are combined.

The present invention is not limited to the embodiment described above, and various modifications can be made without departing from the spirit of the present invention as a matter of course.

REFERENCE SIGNS LIST 10 learning apparatus
12 communication unit 14 first database
16 second database
18 operation unit
20 CPU
22 RAM
24 ROM
26 display unit
31 input image
32A input layer
32B intermediate layer
32C output layer
34 loss value calculation unit
35 mask data
36 parameter control unit
37 coordinate information
38 mask data creation unit
S10 to S28 step

What is claimed is:

1. A learning apparatus comprising:
a memory that stores a first image set in which a first image for learning and coordinate information for identifying a region larger than a region of interest included in the first image are associated with each other and a second image set in which a second image for learning and second mask data for identifying a region of interest included in the second image on a per pixel basis or on a per block-of-pixels basis are associated with each other; and
a processor, configured to:
input the first image to a neural network and obtain a first feature map output from the neural network;
compare the first feature map with the coordinate information associated with the first image to calculate a first loss value;
update a plurality of parameters of the neural network on the basis of the first loss value;
obtain the second image and the second mask data from the second image set;
input the second image to the neural network and obtain a second feature map output from the neural network;
compare the second feature map with the second mask data associated with the second image to calculate a second loss value; and
update the plurality of parameters of the neural network on the basis of the second loss value.

2. The learning apparatus according to claim 1, wherein the processor is further configured to:
create first mask data on the basis of the coordinate information associated with the first image, wherein
the first mask data corresponding to the first image is created before the first image is input to the neural network.

3. The learning apparatus according to claim 1, wherein the coordinate information is information for identifying a rectangular region that includes the region of interest, and the first mask data is mask data in which the rectangular region is masked.

4. The learning apparatus according to claim 3, wherein a region smaller than the rectangular region is set within the rectangular region, and
the processor excludes a region that is within the rectangular region and outside the region smaller than the rectangular region from loss value calculation.

5. The learning apparatus according to claim 3, wherein a region smaller than the rectangular region is set within the rectangular region, and
the processor excludes the region smaller than the rectangular region from loss value calculation.

6. The learning apparatus according to claim 1, wherein the coordinate information is information for identifying an elliptic region that includes the region of interest, and the first mask data is mask data in which the elliptic region is masked.

7. The learning apparatus according to claim 6, wherein a region smaller than the elliptic region is set within the elliptic region, and
the processor excludes a region that is within the elliptic region and outside the region smaller than the elliptic region from loss value calculation.

8. The learning apparatus according to claim 6, wherein a region smaller than the elliptic region is set within the elliptic region, and
the processor excludes the region smaller than the elliptic region from loss value calculation.

9. The learning apparatus according to claim 1, wherein the processor compares the first feature map smaller in size than the first image with the first mask data smaller in size than the first image to calculate the first loss value, and
the processor compares the second feature map smaller in size than the second image with the second mask data smaller in size than the second image to calculate the second loss value.

10. The learning apparatus according to claim 1, wherein in the first image set, the first image that includes a blur is present.

11. The learning apparatus according to claim 1, wherein the first image that constitutes the first image set and the second image that constitutes the second image set are medical images.

12. The learning apparatus according to claim 1, wherein the first image that constitutes the first image set is an image extracted from a moving image.

13. The learning apparatus according to claim 1, wherein the first image that constitutes the first image set and the second image that constitutes the second image set are images captured by an endoscope apparatus.

14. The learning apparatus according to claim 1, wherein the second mask data is mask data in which a lesion region included in the second image is masked.

15. A learning apparatus comprising:
a memory that stores a first image set in which a first image for learning and first mask data for identifying a region larger than a region of interest included in the first image are associated with each other and a second image set in which a second image for learning and second mask data for identifying a region of interest included in the second image on a per pixel basis or on a per block-of-pixels basis are associated with each other; and
a processor, configured to:
input the first image to a neural network and obtain a first feature map output from the neural network;
compare the first feature map with the first mask data associated with the first image to calculate a first loss value;
update a plurality of parameters of the neural network on the basis of the first loss value;
obtain the second image and the second mask data from the image set;
input the second image to the neural network and obtain a second feature map output from the neural network;

compare the second feature map with the second mask data associated with the second image to calculate a second loss value; and update the plurality of parameters of the neural network on the basis of the second loss value.

16. The learning apparatus according to claim 1, wherein each of the first mask data and the second mask data is mask data that is subjected to a pooling process at least once.

17. The learning apparatus according to claim 16, wherein the neural network has at least one pooling layer, and
each of the first mask data and the second mask data is mask data that is subjected to a pooling process corresponding to the pooling layer.

18. A learning method comprising:
preparing a first image set in which a first image for learning and coordinate information for identifying a region larger than a region of interest included in the first image are associated with each other and a second image set in which a second image for learning and second mask data for identifying a region of interest included in the second image on a per pixel basis or on a per block-of-pixels basis are associated with each other;
inputting the first image to a neural network and obtaining a first feature map output from the neural network;
comparing the first feature map with the coordinate information associated with the first image to calculate a first loss value;
updating a plurality of parameters of the neural network on the basis of the first loss value;
obtaining the second image and the second mask data from the second image set;
inputting the second image to the neural network and obtaining a second feature map output from the neural network;
comparing the second feature map with the second mask data associated with the second image to calculate a second loss value; and
updating the plurality of parameters of the neural network on the basis of the second loss value.

19. A learning method comprising:
preparing a first image set in which a first image for learning and first mask data for identifying a region larger than a region of interest included in the first image are associated with each other and a second image set in which a second image for learning and second mask data for identifying a region of interest included in the second image on a per pixel basis or on a per block-of-pixels basis are associated with each other;
inputting the first image to a neural network and obtaining a first feature map output from the neural network;
comparing the first feature map with the first mask data associated with the first image to calculate a first loss value;
updating a plurality of parameters of the neural network on the basis of the first loss value;
obtaining the second image and the second mask data from the image set;
updating a plurality of parameters of the neural network on the basis of the first loss value;
obtaining the second image and the second mask data from the image set;
inputting the second image to the neural network and obtaining a second feature map output from the neural network;
comparing the second feature map with the second mask data associated with the second image to calculate a second loss value; and
updating the plurality of parameters of the neural network on the basis of the second loss value.

* * * * *